United States Patent
Elbaum et al.

(10) Patent No.: US 7,127,094 B1
(45) Date of Patent: Oct. 24, 2006

(54) METHOD OF CONTROLLING DATA GATHERED AT REMOTE LOCATIONS

(75) Inventors: Marek Elbaum, Dobbs Ferry, NY (US); Adam Jacobs, Woodcliff Lake, NJ (US); Nikolai Kabelev, Irvington, NY (US); Sunguk Keem, Norwood, NJ (US)

(73) Assignee: Electro Optical Sciences Inc, Irvington-on-Hudson, NY (US)

( * ) Notice: Subject to any disclaimer, the term of this patent is extended or adjusted under 35 U.S.C. 154(b) by 798 days.

(21) Appl. No.: 10/336,025

(22) Filed: Jan. 2, 2003

(51) Int. Cl.
*G06K 9/00* (2006.01)

(52) U.S. Cl. .................................................. 382/128

(58) Field of Classification Search ................ 382/128, 382/132, 133, 134; 128/922; 705/2
See application file for complete search history.

(56) References Cited

U.S. PATENT DOCUMENTS

| | | | | |
|---|---|---|---|---|
| 5,291,560 A | * | 3/1994 | Daugman | ..................... 382/2 |
| 5,297,034 A | * | 3/1994 | Weinstein | .............. 364/413.02 |
| 6,014,451 A | * | 1/2000 | Berry et al. | ................ 382/110 |
| 6,081,612 A | * | 6/2000 | Gutkowicz-Krusin et al. | ............... 382/128 |
| 6,115,486 A | * | 9/2000 | Cantoni | ..................... 382/128 |
| 2001/0014167 A1 | * | 8/2001 | Gifford et al. | ............. 382/117 |
| 2001/0026632 A1 | * | 10/2001 | Tamai | ........................ 382/116 |
| 2002/0164059 A1 | * | 11/2002 | DiFilippo et al. | ........... 382/128 |

* cited by examiner

*Primary Examiner*—Andrew W. Johns
(74) *Attorney, Agent, or Firm*—Rodney T Hodgson

(57) ABSTRACT

Data corresponding to biological tissue or lesions imaged in a remote location are communicated automatically to a central location, where the data are analyzed using data and algorithms stored securely at the central location. A result of the analysis is communicated from the central location to the remote location. Payment to an entity associated with the central location is made for each image or set of images.

22 Claims, 1 Drawing Sheet

METHOD OF CONTROLLING DATA GATHERED AT REMOTE LOCATIONS

FIELD OF THE INVENTION

The field of the invention is the field of business methods, applied in particular to the field of medical imaging.

OBJECTS OF THE INVENTION

It is an object of the invention to provide a business method for providing security and confidentiality of data from imaging of tissue used for diagnosing medical conditions.

It is an object of the invention to provide a method for collecting payment for diagnosing medical conditions from imaging of tissue.

It is an object of the invention to provide a method for providing calibration checks and system checks of medical imaging systems located remotely from a central location.

It is an object of the invention to provide a method for reducing the amount of data communicated between a remote location and a central location.

It is an object of the invention to provide a method for providing improvements to a database in a central location using data collected in a remote location.

SUMMARY OF THE INVENTION

Data corresponding to tissue or lesions imaged in a remote location are communicated automatically to a central location, where the data are automatically manipulated and analyzed using data and algorithms stored at the central location. A result of the analysis is communicated automatically from the central location to the remote location. Payment to an entity associated with the central location may be made for each image or set of images. The result of the analysis is used by a practitioner associated with the remote location in diagnosis and treatment of the patient imaged. Results of the diagnosis and treatment may be communicated to the central location to update the database and algorithms in the central location.

DETAILED DESCRIPTION OF THE INVENTION

Figure 1:
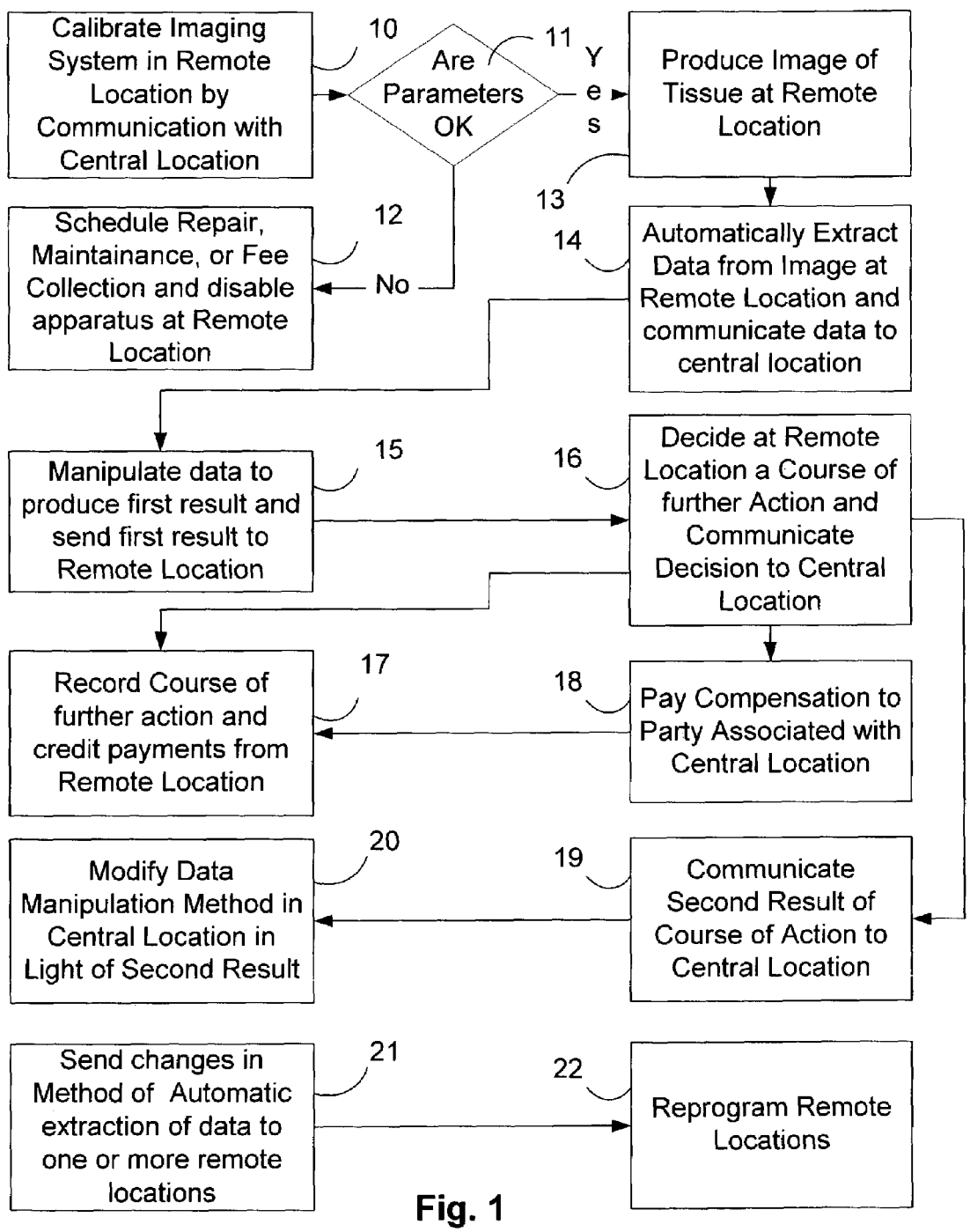
FIG. 1 is a flow chart of the method of the invention.

Patents assigned to the assignee of the present invention describe in great detail systems which image biological tissue and teeth. In particular, the images may be automatically reduced to data sets, and the data sets used as a diagnosis tool to aid professional practitioners in diagnosis and treatment of medical conditions. In particular, US patent teaches a way to tell if a skin lesion is melanoma. The data sets from many lesions must be scanned and the results of biopsies of the lesions entered into a database to extract the predicting features from the data of any one image. Thus, the results of many expensive images and more expensive procedures and biopsies are vital to the business of producing and selling imaging systems. The data and algorithms for using the data may be stored in a computer in the location where the images are taken. However, such data are hard to keep confidential and vulnerable to misappropriation by unauthorized people. In addition, a business model where payment is made for each image processed is hard to enforce without an accurate count of images made, and the accurate count is subject to manipulation at a remote site.

The following U.S. patent applications: U.S. application Ser. No. 08/778,001 filed Dec. 31, 1996 (now U.S. Pat. No. 6,201,880 issued Mar. 13, 2001); U.S. application Ser. No. 09/031,929 filed Feb. 27, 1998 (now U.S. Pat. No. 6,081,612 issued Jun. 27, 2000); U.S. application Ser. No. 09/032,450 Feb. 27, 1998 (now U.S. Pat. No. 6,208,749 issued Mar. 27, 2001); U.S. application Ser. No. 09/467,344 filed Dec. 20, 1999 (now U.S. Pat. No. 6,282,359 issued Aug. 28, 2001); U.S. application Ser. No. 09/467,345 filed Dec. 20, 1999; U.S. application Ser. No. 09/604,645 filed Jun. 27, 2000 (now U.S. Pat. No. 6,307,957 issued Oct. 23, 2001); U.S. application Ser. No. 09/670,492 filed Sep. 26, 2000; U.S. application Ser. No. 09/722,248 filed Nov. 24, 2000 (now U.S. Pat. No. 6,341,957 issued Jan. 29, 2002); U.S. application Ser. No. 09/944,248 filed Aug. 31, 2001; U.S. application Ser. No. 09/991,897 filed Nov. 23, 2001; and U.S. application Ser. No. 10/071,277 filed Feb. 8, 2002, are assigned to the assignee of the present invention and describe in great detail apparatus and methods for imaging and diagnosing of teeth and tissue. The above identified patents, patent applications, and references, including the references included therein, are included herein in their entirety by reference.

The U.S. Pat. No. 6,081,612, noted above, describes in great detail how an image of a skin lesion may be treated to decide if the skin lesion is melanoma or if it is a look-alike nevus. The application describes how the image is generated in a number of spectral bands, how the image is segmented, and how the segmented images from each spectral band are used to generate a number of features. Some of these features, among others, are the ellipticity, blochiness, color, area, edge definition, etc. Each of the forgoing features may be reduced to a single number, and each may be used as a classifier to distinguish melanoma from look alike lesions.

The actual features used in the decision process must be chosen from a very great number of features for a large number of lesions. At first, lesions are imaged, and then the lesions excised and diagnosed by a pathologist. With a large number of melanoma and non-melanoma samples, an algorithm for classifying the lesions may be worked out. The process of imaging and diagnosis to work out the algorithm is very expensive and time consuming.

Presently, a stand alone imaging system connected with a computer which has been programmed with the correct algorithm and contains the data have predicted from the images in a blind test that a lesion is melanoma with 97% sensitivity and 68% specificity. The data in the stand alone computer is, however, neither confidential nor secure.

The method of the invention takes images or data from images at a remote location and communicates the data automatically to a central location. FIG. 1 shows a block diagram of embodiments of the invention. An optional first step 10 has the central location checking whether the parameters of the remotely located apparatus are within specified limits. The uniformity of the illumination, the signal to noise ratio of the image recording device, etc are queried. While the remote location can perform calibration and control steps and shut itself down if necessary, more control may be practiced in the central location step 10. If the decision step 11 shows some parameter outside of specifications, or if, for example, required fees have not been paid, the remote location may be disabled, and maintainence and repair or fee collection scheduled. If the calibration check is OK, the apparatus in the remote location is used to produce one or more images of biological tissue in step 13. In the case of the melanoma detection unit noted above, an image of a lesion on the skin of the patient is obtained with a hand held unit about the size and shape of a telephone handset. Other types of in vivo imaging systems, such as endoscopes or tooth transillumination images are also anticipated by the inventor. Other types of tissue, for example histopathological slides of normal and/or abnormal tissue, may be imaged in vitro.

The data from the image or images is automatically manipulated at the remote location in step 14 to extract features and data, which is then communicated to the central location. Note that many megabytes of information are normally contained in each image, and communication times are too long to transmit even a fraction of the image data from the remote location to the central location. For the melanoma detection or for other in vivo and in vitro image analysis anticipated by the inventor, only a few hundreds or thousands of numbers are required.

The central location computer contains the algorithms needed to manipulate the data for diagnosis in step 15, and can be kept much more secure. At the central location, the data from the remote location is automatically analyzed, and the result of the analysis is automatically sent back to the remote location to assist the practitioner associated with the remote location in diagnosis in step 16. The practitioner located at the remote location decides on a course of further action, for example, to biopsy the lesion in a suspected melanoma and send a specimen to a pathologist for inspection. The practitioner may report back to the central location the course he has chosen in step 17, where the course is recorded.

The method of the invention also offers the possibility of a reliable method of collecting fees in step 18 for the work involved in collecting the data and/or providing the system needed for the imaging and analysis. For example, for each image, lesion, or patient analyzed, an invoice may be generated and transmitted to the remote location. As an alternative, the remote location may keep a balance in an account with the central location, and the balance debited for each image, lesion, or patient analyzed. Alternatively, a credit card number could be transmitted for each transaction, and the credit card account debited. This procedure would be especially valuable if the images were taken by the patient himself or herself, at a location remote from a practitioner. Imaging systems could be installed, for example, in neighborhood drugstores, and a person could scan a suspicious spot, wart, or mole and have the machine give a predicted probability of melanoma. Patients would then be spared the expense of a doctor's office visit.

Collection for each image or patient would also allow the apparatus to be given to the remote location at no cost, or for a modest rental, to the practitioner at the remote location.

The method of the invention is especially valuable in that the amount of information communicated between the remote and the central location may be very much less than the amount of information contained in a single image at a single wavelength. The number of features produced in the data reduction from the image may be in the hundreds or thousands. The images may contain many millions of bytes of information. In any case, the data transmitted may be much less than the data normally transmitted if a full image, or even a compressed image, is transmitted. Typically, the data transmitted is less than one, two, or three orders of magnitude less than the data recorded in the full image. In particular, an amount of data transmitted is less than the amount of data which would be needed to reconstruct an image which would be recognizable by an average human observer as the same image as the original.

The method of the invention also allows for updating the database and the method of manipulating data stored in the central location. The results of the course of further action are communicated from the remote to the central location in step 20, and the central location may change the method of manipulation as more data is gathered. As more data is gathered, it is expected that the sensitivity and specificity of the results will increase. Any deviation from the predicted result could be used to update the central location database using stored data about the image or using the stored images themselves. Higher sensitivity will be critical in competition with other systems, and the possibility of refining the database and statistical record keeping for the entire database is crucial.

The method of the invention also allows for updating the database and the method of imaging and data reduction in the remote location. In particular, the updating of the remote location could be carried out in step 21 at the same time as the updating of very many remote locations by a single command sent out from the central location over the internet. In step 22, the apparatus in the remote locations is shown to be reprogrammed.

In an alternative embodiment of the invention, sufficient information is stored at the remote location to generate a result from the full image data. The reduced image data is sent to the central location as before, where the data is manipulated to produce a result which is communicated to the remote location. If the two results are the same, a course of action is recommended. If the two results are different, another course of action is recommended.

It is critical that the apparatus be checked very often to check the illumination systems, the optical system, and the image recording apparatus. Commands from the central location to the remote location are thus used, and no result is returned to the remote location if the calibration has not been done or if any parameter such as signal to noise ratio of the imaging system or lighting uniformity is out of range. In fact, such calibration and checking is preferably done before images are obtained, and if the apparatus is out of range or specification, the apparatus may be shut down automatically by communication from the central location. In fact, one of the criterion could be whether the remote location has paid for previous images, or has enough credit allowed for future images. In case the payment criteria are not met, the apparatus is shut down.

Obviously, many modifications and variations of the present invention are possible in light of the above teachings. It is therefore to be understood that, within the scope of the appended claims, the invention may be practiced otherwise than as specifically described.

The invention claimed is:

1. A method, comprising:
   a) producing an image of biological tissue at a first remote location; then,
   b) automatically extracting data from the image to generate a first data set, wherein data in the first data set is insufficient to produce a representation of the image recognizable by an average person; then,
   c) automatically communicating the first data set to a central location; then,
   d) automatically manipulating the first data set at the central location to produce a first result, the manipulation method kept as a confidential method in the central location;

e) automatically communicating the first result to the first remote location; then
f) deciding at the first remote location a first course of further action based on the first result; and then
g) communicating a second result from the first remote location to the central location, where the second result is the result of the first course of further action.

2. The method of claim 1, further comprising;
h) modifying the manipulation method on the basis of the second result and the first data set.

3. The method of claim 1, wherein the first course of further action is an excision of tissue.

4. The method of claim 3, further comprising:
pathologically classifying the excised tissue.

5. The method of claim 1, wherein compensation is paid to a party associated with the central location.

6. The method of claim 5, wherein image producing equipment is provided by a party associated with the central location at no cost to parties at the first remote location.

7. The method of claim 5, wherein compensation is paid for each result transmitted from the central location to the first remote location.

8. The method of claim 5, wherein image producing equipment is provided by a party associated with the central location for a rental fee.

9. The method of claim 5, wherein image producing equipment is disabled by command from the central location if compensation is not paid to the party associated with the central location.

10. The method of claim 1, wherein the step a) of producing an image comprises:
$a_1$) calibrating an imaging system at the first remote location by command from the central location;
$a_2$) producing the image with the calibrated imaging system.

11. The method of claim 10, wherein image producing equipment is disabled by command from the central location if the calibration step reveals an out of range parameter.

12. The method of claim 1, where the image of biological tissue is an image of an in vivo lesion in biological tissue.

13. The method of claim 1, where the image of biological tissue is an image of in vitro biological tissue.

14. The method of claim 1, where the method of automatically extracting data from the image can be changed by communication between the central location and the first remote location.

15. The method of claim 14, where the method of automatically extracting data from the image can be changed by simultaneous communication between the central location and a plurality of remote locations.

16. A method, comprising:
a) producing an image of biological tissue at a first remote location, then
b) automatically extracting data from the image at the first remote location to generate a first data set, wherein the amount of information in the first data set is at least one thousand times less than the amount of information contained in the image; then
c) communicating the first data set to a central location; then,
d) automatically manipulating the first data set in the central location to produce a first result; then,
e) communicating the first result to the remote location; then
f) deciding at the first remote location a first course of further action based on the first result; and then
g) communicating a second result from the first remote location to the central location, where the second result is the result of the first course of further action.

17. The method of claim 16, further comprising:
f) automatically manipulating the first data set in the first remote location to produce a second result;
g) comparing the first result with the second result at the remote location; and
h) if the first result and the second result are equal, displaying at the first remote location a first recommended course of further action; or
i) if the first result and the second result are unequal, displaying at the remote location a second recommended course of further action.

18. The method of claim 16, wherein the steps a and b are carried out in a hand held imaging device.

19. The method of claim 18, wherein the handheld imaging device may be reprogrammed by communication from the central location.

20. The method of claim 18, wherein the handheld imaging device may be calibrated by communication from the central location.

21. The method of claim 18, wherein the central location automatically records each time an image is produced.

22. The method of claim 18, wherein the central location periodically produces an invoice detailing the recorded images.

* * * * *